United States Patent [19]

Tepic

[11] Patent Number: 4,530,114
[45] Date of Patent: Jul. 23, 1985

[54] TOTAL HIP JOINT PROSTHESES

[76] Inventor: Slobodan Tepic, 6 Sermageova, 41000 Zagreb, Yugoslavia

[21] Appl. No.: 398,842

[22] Filed: Jul. 16, 1982

[51] Int. Cl.³ .......................... A61F 1/04; A61F 5/04
[52] U.S. Cl. .................................. 623/23; 128/92 C; 128/92 CA
[58] Field of Search .................. 3/1, 1.9, 1.91, 1.911, 3/1.912, 1.913; 128/92 R, 92 B, 92 BB, 92 BC, 92 C, 92 CA, 92 D

[56] References Cited

U.S. PATENT DOCUMENTS

| | | | |
|---|---|---|---|
| 2,765,787 | 11/1956 | Pellet | 128/92 CA |
| 3,846,846 | 11/1974 | Fischer | 3/1.913 |
| 3,987,499 | 10/1976 | Scharbach et al. | 128/92 C |
| 4,129,903 | 12/1978 | Huggier | 3/1.913 |
| 4,187,559 | 2/1980 | Grell et al. | 3/1.91 |
| 4,227,518 | 10/1980 | Aginsky | 128/92 BC |
| 4,406,023 | 9/1983 | Harris | 3/1.912 |

FOREIGN PATENT DOCUMENTS

| | | | |
|---|---|---|---|
| 2425237 | 1/1980 | France | 3/1.913 |

Primary Examiner—Richard J. Apley
Assistant Examiner—David J. Isabella
Attorney, Agent, or Firm—Cesari and McKenna

[57] ABSTRACT

Joint prosthesis for implantation in a human or animal body comprises a joint member for mounting to a bone. Flexible tension transmitting wires are connected at their one ends to the joint member at a first location thereon, the ends of the wires being anchored in the bone at a location therein normally subjected to tensile forces. A compression transmitting member has one end portion coupled to the joint member at a second location thereon different from the first location and its opposite end portion is anchored in said bone at a location therein normally subjected to compression forces. The coupling to the compression transmitting member is such that only compressive forces are coupled to that member from the joint member. The components of the prosthesis are arranged to emulate as closely as possible the natural bone structure so that the forces exerted on the remaining bone approximate those applied to the normal bone.

39 Claims, 15 Drawing Figures

TOTAL HIP JOINT PROSTHESES

This invention relates to body joint prostheses and, especially, prostheses for use in an artificial hip joint and to a method of and tool for implanting same.

BACKGROUND OF THE INVENTION

An artificial hip joint comprises a femoral component which is essentially a ball mounted at the end of the femur and an acetabular component which is a socket mounted in the hip bone. Hip prosthesis failure is most commonly associated with the loosening of one or both of these components. Loosening alone may be symptomatic in various degrees and may, in itself, be an indication of the necessity of revision or reoperation to correct the problem. Sometimes, however, such loosening may have drastic consequences such as protrusion of the acetabular or proximal femur fracture. Such prosthesis failure can be traced ultimately to two problems. Either the tissue reacts to the prosthetic materials used or the tissue reacts to grossly altered mechanical properties of the prosthesis from the natural bone.

More particularly, the joint components are foreign to the bone tissue and cause some tissue necrosis at the interface with the prosthesis. More damaging to the bone tissue, however, is the polymethylmethacrylate (PMMA) cement which is usually used to fix many conventional prostheses in the bone structure. That cement is a self-polymerizing synthetic plastic whose polymerization gemerates temperatures which are high enough to damage surrounding bone tissue. Moreover, the monomer component of that cement is a toxic substance. Unless there is complete polymerization of the cement components, unbound catalyst monomer remains which can leak into the surrounding bone tissue. In fact, such leakage has already been identified as a major source of PMMA toxicity in patients receiving artificial hip joints.

In order to avoid such problems occasioned by the use of cements, hip joint prostheses have been devised which do not require such cement fixation. Examples of some such prostheses not requiring cement are disclosed, for example, in U.S. Pat. Nos. 4,051,559; 4,080,666; 4,101,985 and 4,187,559.

Prior conventional prostheses, however, do not completely address the loosening phenomenon due to the grossly altered mechanical properties of the implant and the nonphysiological nature of the application of force from the implant to the bone. One good exposition of that problem is contained in the aforementioned U.S. Pat. No. 4,187,559. However, the femoral prosthesis described in that reference is not completely satisfactory because it does not take into account the entire structural nature of the bone receiving the implant with the result that the implant is not really the mechanical equivalent of its natural counterpart. Consequently, that prior implant creates unnatural stresses in the remaining bone structure which tends to cause long-term deterioration of the bone and loosening of the implant. A brief explanation of the structure of the femur will now be given with reference to FIGS. 1, 2 and 2A of the accompanying drawings.

Figure 1:
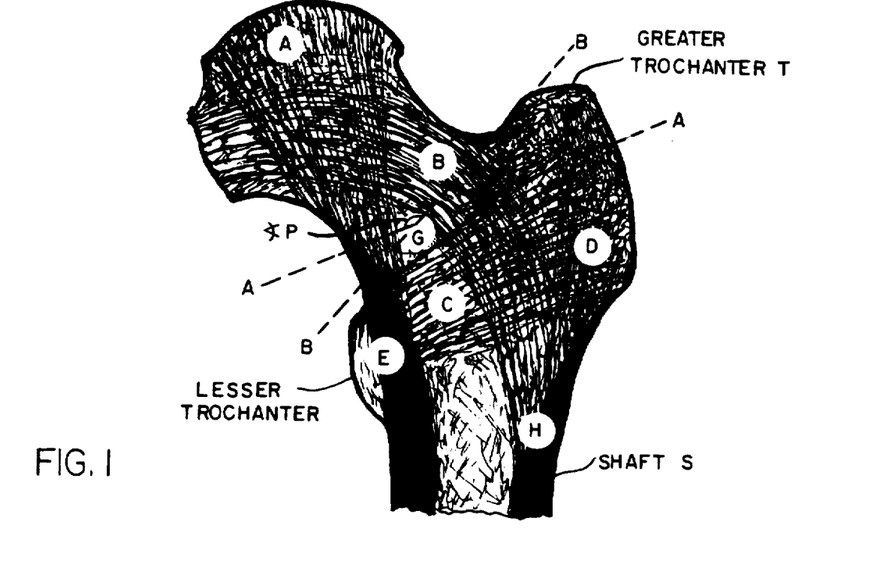
FIG. 1 is a cross-sectional view illustrating the proximal end of a femur.

FIG. 1 illustrates the internal structure of the proximal femur (see Color Atlas of Human Anatomy by R. M. McMinn and R. T. Hutchings, page 275). The shaft S branches into a head which is the ball component of the natural hip joint and the so-called greater trochanter which is a protrusion on the lateral side of the femur. The major groups of structural units of the cancellous bone (trabeculae) are identified in that figure as follows:

(A) those from the medial surface of the shaft to the head;

(B) those from the lateral surface of the shaft to the head;

(C) those from the medial surface of the shaft to the greater trochanter;

(D) those from the lateral surface of the shaft to the greater trochanter;

(E) the calcar femorale which is a dense concentration of trabeculae extending from the region of the lesser trochanter to the undersurface of the neck;

(G) a triangular area of few trabeculae; and (H) the region of attachment of trabeculae groups B and D to the lateral side of the femur shaft.

Figures 2, 2A:
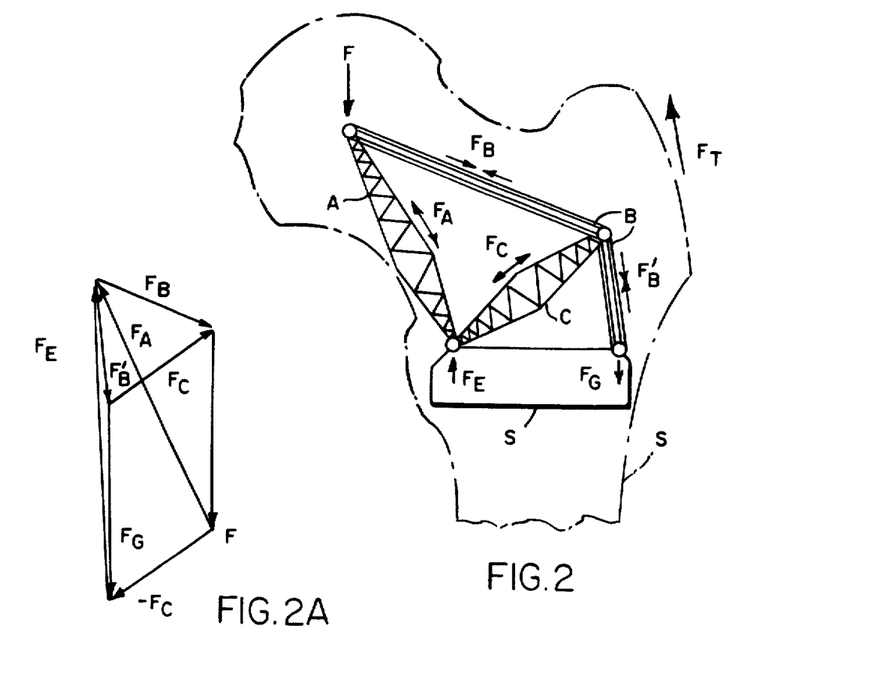
FIG. 2 is a diagrammatic view showing the distribution of forces applied to the proximal end of the femur under a normal load.
FIG. 2A is a vector diagram of the reactions to the femur load.

FIG. 2 illustrates a simplified and useful structural analogy to the bone structure at the upper end of the femur illustrated in FIG. 1. The system is statically determinate and the reactions to the applied force F follow from the vector diagram shown in FIG. 2A. Truss elements A and C which correspond to the femur trabeculae A and C described above are loaded in compression, while cables B corresponding to trabeculae B are loaded in tension. Reaction forces $F_E$ and $F_G$ are transferred to the support S corresponding to the femur stem S. From these figures, it is clear that the medial side of the femur cortical shell will be loaded in compression, while its lateral side will be loaded in tension. Force $F_T$ which is applied in nature by muscles attached to the greater trochanter and through trabeculae D will add to the tensile loading of the lateral side of the femur as well as to compressive loading of trabeculae C.

The designs of commercially available femoral prostheses are very similar. They all comprise a ball or head connected by way of a neck to a long stem or shaft which is inserted deep into the femoral intramedullary canal to support the head at the proximal end of the femur. The variations from one prosthesis to another are related primarily to the choice of stem design. In all of these designs, including the one described in the above-mentioned U.S. Pat. No. 4,187,559, the long metal stem of the prosthesis is orders of magnitude stiffer than the replaced material, i.e. the soft cancellous bone and marrow of the intramedullary canal. Therefore, the stress patterns in the upper femur are significantly altered by the implant. Also, under load, a force couple is imparted to the femur which is transmitted to the opposite walls of the cortical tube in directions perpendicular to the trabeculae. These forces do not promote bone growth and unduly stress the walls of the femur, sometimes causing fractures thereof.

The concept of using a rigid stem inserted deep into the intramedullary canal to transfer loads from the artificial joint to the femur is inherently destructive to the bone and probably arose initially due to the appealing simplicity of prosthesis insertion. However the presence of the rigid prosthesis stem in the femur causes drastic changes in the stress distributions in the altered bone which strongly prejudice long-term success of the joint replacement. While improvement of component materials and the design of such implants has more or less solved the problem of prosthesis stem fracture, stem loosening and bone fracture have surfaced as the major long-term complications inherent in hip joint replacement.

SUMMARY OF THE INVENTION

Accordingly, the present invention aims to provide prostheses which can be implanted in bone structure without requiring cement fixation.

Another object of the invention is to provide prostheses which minimize changes in the mechanical properties of the remaining structure of the bone in which they are implanted.

A further object of the invention is to provide a prosthesis of this type which matches the mechanical impedances at the interfaces between the prosthesis and the remaining bone.

Another object of the invention is to provide such a prosthesis which, in use, applies more or less the same forces to the remaining bone structure as did the natural joint component which it replaces.

Still another object of the invention is to provide a hip joint prosthesis which is designed for immediate fixation so that the patient is ambulatory in a minimum amount of time.

Yet another object of the invention is to provide a hip joint prosthesis which is composed of a few relatively simple components which are easy to manufacture and implant in the patient.

Another object is to provide an improved method of implanting prostheses in bone.

A further object is to provide a tool to facilitate the implantation of prostheses and the application of fixation wire used in bone surgery.

Other objects will, in part, be obvious and will, in part, appear hereinafter.

The invention accordingly comprises the sequence of steps and the features of construction, combination of elements and arrangement of parts which will be exemplified in the following detailed description, and the scope of the invention will be indicated in the claims.

Generally, the hip joint prostheses described herein provide load transfer from the prostheses to the supporting bone structures in a more natural way than prior prostheses, giving better chances for the long-term survival of the implants and of the bones themselves. One femoral prosthesis made in accordance with this invention comprises four main parts and a number of anchoring wires or cables. These parts include a base plate which covers the proximal end of the femur over two cut planes on the femur formed by transsection of the femur head. The lateral end of the base plate is anchored to the femur by a plurality of long thin anchoring wires which are driven into the medullary canal at the lateral side of the femoral shaft. Thus, the anchoring wires emulate the trabeculae B which, as described above, are normally under tension.

The second component of the prosthesis is a generally cylindrical, relatively short compression screw which is turned down through a threaded opening in the medial end of the base plate into the medullary canal where it threadedly engages the medial aspect of the femoral cortical tube. This screw substitutes for the aforementioned trabeculae A which are normally under compression. The trabeculae C, which, as noted above, are also under compression, are emulated by the base plate itself whose lengthwise extent corresponds generally to the orientation of trabeculae C.

The third component of the femoral prosthesis is a head member consisting of a head with a depending neck and shoulder. The underside of the shoulder is shaped to seat on the base plate. The lateral side of the head member is keyed to the lateral end of the base plate at the locations of the anchoring wires. The medial side of the head member, on the other hand, is axially decoupled from the plate and pivotally connected by the fourth component of the implant, namely a pin, to the upper end of the compression screw extending above the base plate.

When the head member is placed under a load, the downward force is transmitted by the pin to the compression screw and thence to the medial femoral shaft. Thus, the bone structure at the medial side of the femur is subjected to the same compressive loading as a normal femur. The loading of the head member also exerts a tensile force on the lateral end of the plate and the anchoring wires which force is thereupon transferred to the cortical bone at the lateral side of the femur, thereby approximating the distribution of tensile stresses that are applied by the trabeculae B in the case of the natural bone.

It is important to note that the pin connection between the head member and the compression screw prevents any rotational moments due to the applied load from being coupled from the head member to the screw and thereby to the femur shaft. In other words, the screw is not subjected to force couples that might cock the screw and thereby tend to loosen its threaded connection to the femur and to exert sideways forces on the bone that could fracture the bone.

Thus, the present prosthesis is composed of components which emulate the bone structure removed during arthoplasty or hemiarthoplasty. These components replace only what has actually been removed from the bone. Therefore, the prosthesis minimizes changes in the mechanical properties of the remaining bone structure. Furthermore, the prosthesis matches the mechanical impedances at the prosthesis-bone interfaces so that the remaining bone structure is subjected to more or less the same loads and stresses as in the case of a normal femur. Also, firm implantation is accomplished without requiring any cements. Therefore, fixation occurs immediately so that the patient is ambulatory in a minimum amount of time. Nor is the patient subjected to the toxic effects of the fixating cements conventionally used to anchor the implant to the bone. Yet, the prosthesis is composed of only a few parts which are relatively easy to manufacture and to implant into the patient.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENTS

Figure 3:
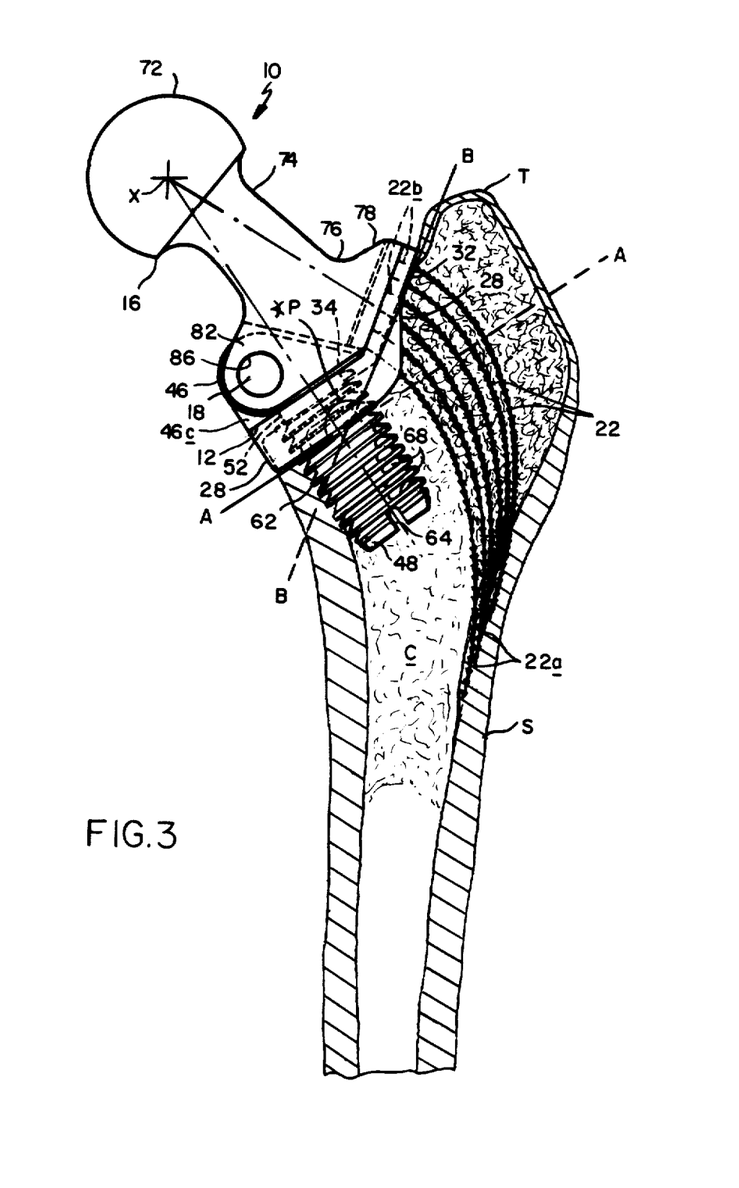
FIG. 3 is a side elevational view with parts in section showing a femoral prosthesis embodying the invention implanted in a femur.
Figure 4:
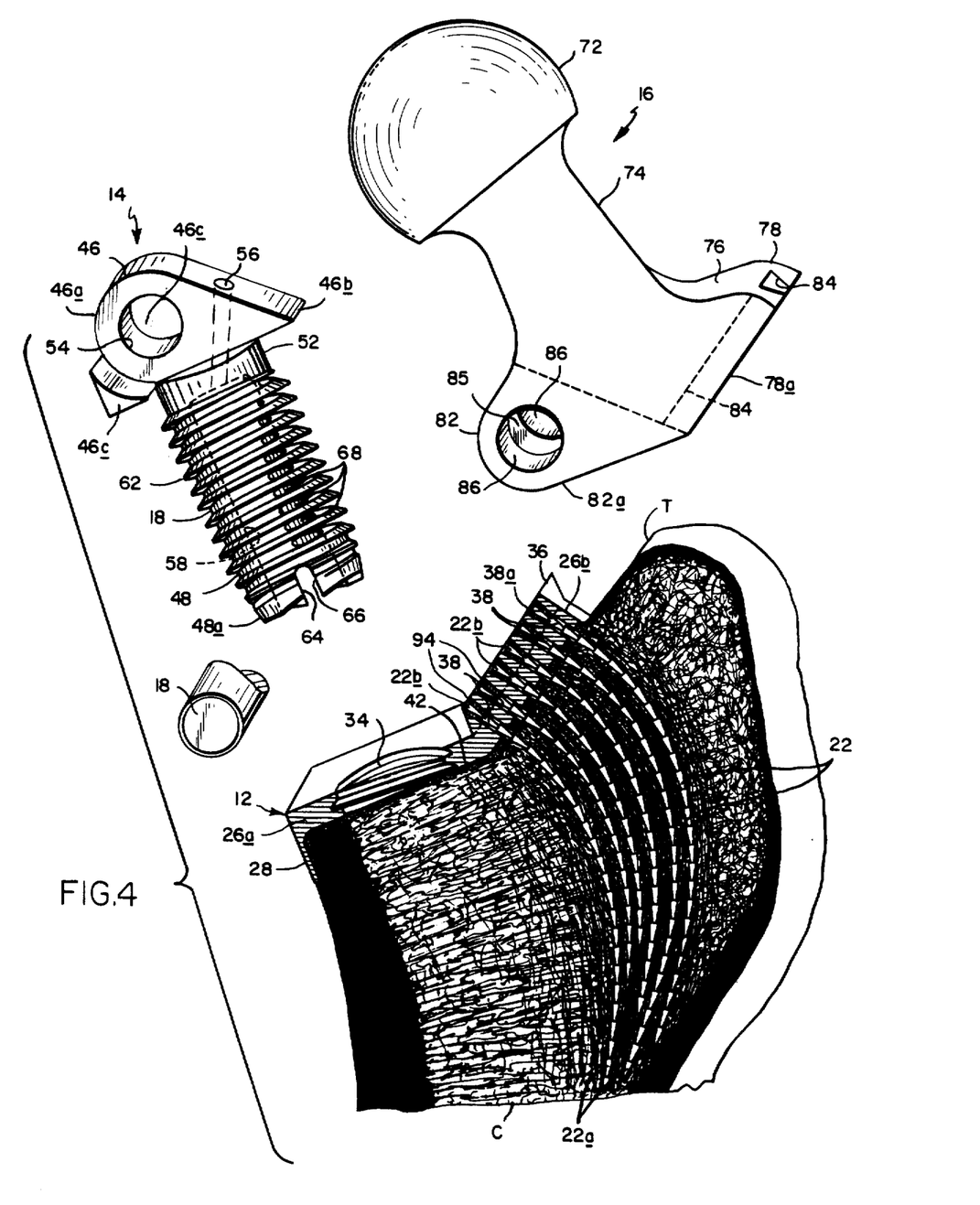
FIG. 4 is an exploded perspective view on a larger scale with some parts in section showing the components of the prosthesis.

FIGS. 3 to 5D illustrate a femur head endoprosthesis indicated generally at 10 embodying the features of this invention. The components of the prosthesis are all made of a biocompatible material such as titanium metal and the external surfaces of those components may be coated with enamel which should also be compatible with the human system. As best seen in FIGS. 3 and 4, the prosthesis 10 is affixed to the proximal end of the femur. Prior to fixation, the natural head of the femur is transsected along the two cut planes A—A and B—B shown in FIG. 1. Plane A—A is more or less perpendicular to the adjacent ends of trabeculae A, while plane B—B is generally perpendicular to the trabeculae B ends. The two planes intersect at femur region G having few trabeculae, with an included angle P of 90° to 180°, and preferably about 110°.

The implant comprises four main parts, namely, a base plate 12 which is seated on the prepared end of the femur, a compression screw 14 which projects through the medial side of the base plate into the femoral medullary canal C, a head member 16 which is connected to the lateral side of the base plate and, by way of a pin 18, to the compression screw. In addition, a set of anchoring wires 22 extend from the lateral side of the base plate into cancellous bone at the lateral side of the femur.

Figure 5A:
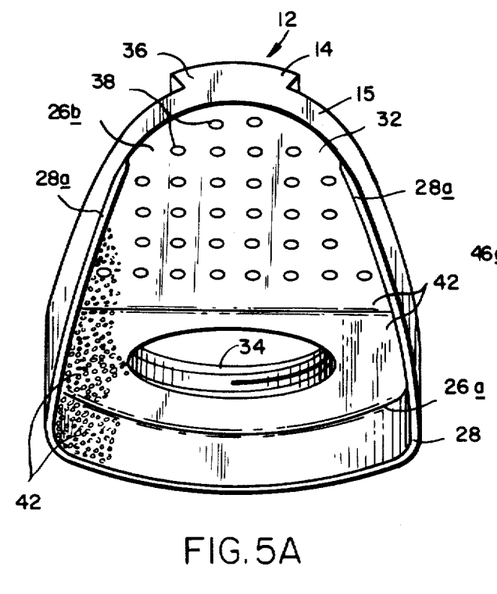
FIGS. 5A to 5D are perspective views with some parts in section showing the prosthesis components in greater detail.

As best seen in FIGS. 4 and 5A, the base plate 12 comprises two planar sections, namely a medial section 26a and a lateral section 26b. The base plate is designed to cover the prepared end of the femur along the two cut planes A—A and B—B respectively as illustrated in FIGS. 1 and 3. Accordingly, the two plate sections 26a and 26b are oriented to define an included angle P which is substantially equal to the included angle between those cut planes, e.g. 110°. A collar 28 depends from plate section 26a all around the free edge of that section. Collar 28 continues along the sides of section 26b gradually decreasing in depth at 28a so that it leaves a relatively wide opening 32 at the lateral end of the base plate.

The plate is adapted to seat flush against the prepared end of the femur, with the collar 28 capturing the femoral medial aspect. The collar opening 32 provides clearance for the greater trochanter T which extends out laterally beyond the plate. Of course, in order to seat the plate properly on the bone, the sides of the femur may have to be trimmed to conform to the outline of the base plate.

A vertical threaded passage 34 for receiving screw 14 is formed through the approximate center of plate section 26a. Also, a key in the form of a male dovetail 36 is provided at the upper surface of the base plate section 26b along the longitudinal axis thereof for anchoring the head member 16 to the plate.

Provided in the plate section 26b is an array of small passages 38 extending entirely through the plate section 26b including its key 36. These passages are arranged in columns and rows so as to be distributed evenly over that section. The openings receive the upper ends of the anchoring wires 22 as will be described in detail later. Finally, the entire underside of base plate 12, including the inside surface of collar 28, which comes into contact with the femur are covered with tiny beads 42. The beads are fused or otherwise strongly bonded to the plate and provide a bone in-growth layer for bone tissue after implantation of the prosthesis.

Figure 5B:
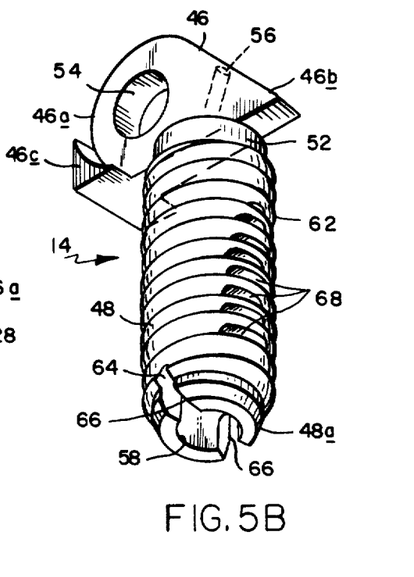

Referring now to FIGS. 4 and 5B, compresion screw 14 comprises a solid head 46 and a shank 48, which is preferably tubular, the two being separated by a neck 52. Head 46 has a generally circular nose portion 46a which protrudes out beyond the medial side of shank 48 and a contiguous generally triangular section 46b which extends out beyond the lateral side of the shank. A small wider triangular filler section 46c depends from the nose section 46a. Sections 46a to 46c have a common lower edge above neck 52 which extends along a line perpendicular to the shank axis. A relatively large lateral pin opening 54 is formed in the nose section 46a. Also, a small passage 56 extends from the upper edge of the head section 46b through that section and through neck 52 into the tubular cavity 58 extending from the free end 48a of shank 48 to the neck 52.

The shank 48 includes an exterior downwardly-cupped right-hand helical thread 62 which runs substantially the entire length of the shank, but not along neck 52 whose diameter, therefore, is less than that of the thread. The shank free end 48a is conical and provided with two or more short, spaced-apart lengthwise slots 64 whose sharp leading side edges form cutting edges 66. Finally, a number of slots 68 are cut through the lateral wall of the shank between the convolutions of thread 62.

The compression screw 14 is designed to be turned clockwise down through opening 34 in base plate 12 and into the cancellous bone at the medial side of the medullary canal as best seen in FIG. 3. As shown there, the screw thread 62 actually bites into the medial side of the cortical shaft S of the femur. The screw-cutting edges 66 facilitate the insertion process by cutting through the cancellous bone inside the cortical tube. Some of that bone tissue enters shank cavity 58 as the screw is turned down into the femur, but can escape through the passage 56 at the top of the screw.

The screw neck 52 is devoid of threads. Accordingly, as soon as the screw is turned down so as to position its neck 52 in the plate opening 34, the screw thread 62 disengages from the plate so that the screw is movable vertically or axially to some extent relative to the plate, but is still fixed thereto in the radial directions. With the screw oriented as in FIG. 3, the slots 68 at the lateral side of the screw are centered more or less along the axis of the cortical tube. These slots perform two main functions. First, they permit the cancellous bone extruded into the shank cavity 58 during the insertion process to fuse with the bone in the intramedullary canal C outside the screw on the lateral side thereof so as to contribute to the fixation of the prosthesis. Secondly, the slots 68 increase the compliance of the lateral side of the screw as compared to the medial side thereof so that downward loads on the screw are transferred to the medial side of the femoral shaft S which is engaged by the noncompliant thread convolutions at the medial side of the screw as shown in FIG. 3.

Further, as shown in FIG. 3, the screw head 46 is shaped so as to provide a strong finished connection point for the head member 16. The head section 46c at the medial side of the screw simply functions as a fillet to occupy the space between the plate and the head member when the prosthesis is assembled as illustrated in that figure.

Figure 5C:
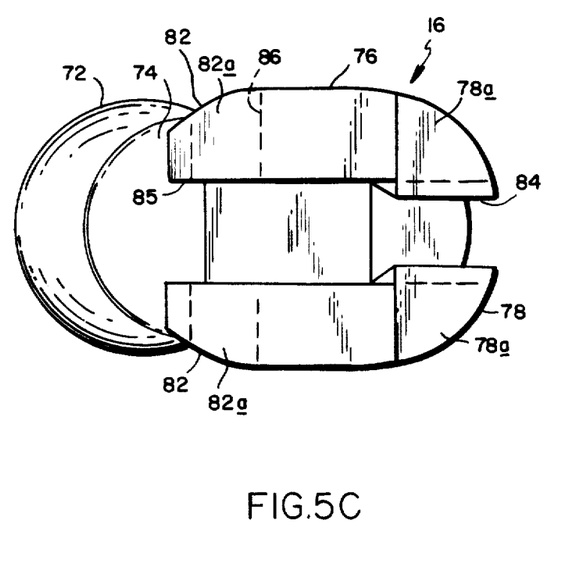

Referring now to FIGS. 4 and 5C, the head member 16 comprises a generally spherical ball or head 72 which is connected by a relatively narrow neck 74 to a shoulder member 76. The head can be sized either as a total prosthesis head which is on the order of 22 to 32 mm. in diameter or as a partial prosthesis head which has a diameter of about 40 to 60 mm. The neck is sized appropriately for strength and range of motion at the hip joint.

The shoulder includes a lateral section 78 which has the same outline as the lateral section 26b of the base plate 26. Extending out from the medial end of shoulder section 78 are a pair of spaced-apart ears 82. The undersurface 78a of section 78 is planar and the undersurfaces 82a of ears 82 define a second plane with the included angle between those planar surfaces corresponding to the angle P between the base plate sections 26a and 26b. A keyway or female dovetail connection 84 is formed at the underside of the shoulder section 78. The keyway extends along the longitudinal center line of that shoulder section and it is aligned with the slot or space 85 between ears 82. Also aligned lateral pin openings 86 are provided through those ears.

Referring now to FIGS. 3 and 4, the head member 16 is attached to base plate 12 and screw 14 by engaging the medial end of the keyway 84 to the lateral end of the base plate key 36 and sliding the head member along the plate until the ears 82 overlie the base plate section 26a with the ear openings 86 aligned with the screw opening 54. The slot 85 between the ears 82 provides clearance for the screw head. When the head member is seated properly, the geometric center X of the head 72 is aligned more or less with the longitudinal center line of screw 14 and lies generally on an imaginary line extending parallel to the upper ends of anchoring wires 22 as shown in FIG. 3.

With the head member 16 properly seated on the base plate 12, the pin 18 is inserted through the aligned openings 54 and 86 in the screw and head member respectively. The pin can be removably retained in place by C-springs (not shown) seated in circular grooves (not shown) in the walls of ear openings 86 just beyond the ends of the pin. When installed, the pin pivotally couples the head member to the screw. When the prosthesis components 12, 14, 16 and 18 are connected together as shown in FIG. 3, there are essentially no voids or gaps between those parts so that the exposed end of the prosthesis has a relatively smooth, finished appearance.

Figure 5D:
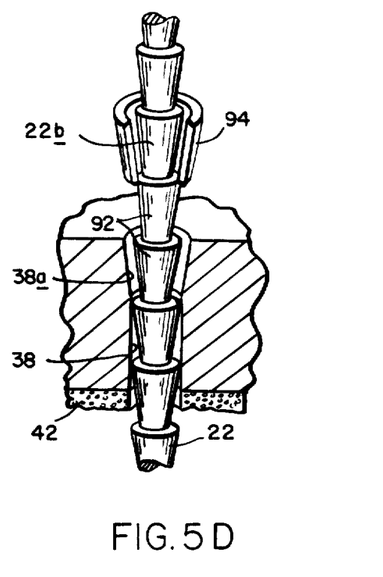

Turning now to FIGS. 4 and 5D, the anchoring wires 22 have fixed lengths and are prebent to correspond approximately to the curvature of the trabeculae B shown in FIG. 1. Each wire is composed of a lengthwise series of generally frustoconical barbs 92 and is received through an opening 38 in the base plate section 26b. The lower end 22a of each wire is pointed to facilitate penetration of the wire down into the lateral side of the femoral medullary canal at the site of the trabeculae B (FIG. 1). The upper end 22b of each wire is secured to the plate 26 by a conical split collar 94 which is engaged around a conical barb 92 above plate 12. Then the wire is pushed further into the femur until the collar 94 wedges in the flared upper end 38a of its passage 38 as best shown in FIG. 4, after which the wire segment 92 above the sleeve is cut away.

The prosthesis is implanted in the bone after transsecting the femur along the cut planes A—A and B—B as shown in FIGS. 1 and 3. Recesses are prepared to receive the base plate 12 of the prosthesis using a router-like power tool equipped with appropriate templet guides. In particular, the cortical tube around the A—A plane is precisely shaped to receive the plate collar 28. Then, to fix the plate to the femur, a few of the wires 22 are driven down through plate openings 38 and into the lateral side of the the femoral tube, preferably by means of a special insertion tool depicted in FIG. 7 and to be described in detail later. The upper ends 22b of those wires are then secured to the plate using the split collars 94 described above, with the segments of those wires projecting above the sleeve being cut flush with the top of the plate section 26b.

The compression screw 14 is then turned down through the threaded plate opening 34 engaging the medial aspect of the cortical tube and the cancellous bone on the lateral side of the medullary canal. As noted previously, the screw edges 66 cut into the bone structure and the threaded engagement with the plate causes the screw to advance down into the femur. The relative positions of the screw thread convolutions and plate opening convolutions produce a controlled amount of compression between the base plate 26 and the femur as the compression screw is driven to its final position. When the screw is inserted completely, the screw neck 52 is positioned in plate opening 34 so that there is no longer threaded engagement between the screw and the plate. Following this, the remaining anchoring wires 22 are implanted to securely anchor the lateral plate section 26a to the proximal end of the femur as shown in FIG. 4.

Next, with the screw 14 oriented so that its nose section 46a faces the medial side of the femur, the head member 16 is assembled by sliding its dovetail connection 84 onto the plate key 36 with the screw nose 46a being received between the head member ears 82. Finally, the pin 18 is inserted through the ears and screw head as shown in FIG. 3 to complete the implant.

A comparison of FIGS. 1 and 3 shows that the head member 16 acting through pin 18 and screw 14, on the one hand, and the anchoring wires 22, on the other, transfers the two main components of the load F (FIG. 2). Such comparison illustrates quite graphically that the anchoring wires 22 replace some of, and load the rest of, the trabeculae B. The tensile component of load F is transferred by way of the head member; base plate and anchoring wires to the remaining trabeculae B and to the cortical bone at the lateral side of the shaft, approximating the distribution of tensile stresses in the natural femur.

The head member 16 also transfers the compressive component of force F via pin 18 and screw 14 to the calcar and the cortical bone at the medial side of the shaft S, as is done in the natural joint by trabeculae A. Pin 18 is aligned with the thread convolutions on the medial side of screw 14, while the thread convolutions on the lateral side of that screw are compliant because of slots 68. Therefore, very little compressive force is transferred to the cancellous bone at the lateral side of the screw in the femur region G (FIG. 1) where only a few trabeculae are present to absorb stress.

Pin 18 supports the head member 16 and functionally replaces the trabeculae C. The reaction of the pin 18 to the tensile forces in the head member is transferred to the cortical bone at the medial side of the shaft by way of the base plate 12. Due to the fact that pin 18 provides a pivotal connection between the head member 16 and screw 14, only compressive forces are coupled to the screw. No torque is applied to the screw tending to cock or tilt the screw within the cortical tube. Moreover, the screw is relatively short. Therefore, very little lateral or outward stress is applied to the tube wall that might tend to cause fractures or breaks in the femur.

Thus this prosthesis emulates in a one-to-one manner the physical locations and functions of the natural structural components of the femur, the patterns of load transfer therein and the resulting stresses in the proximal femur. Therefore, the present prosthesis closely resembles the proximal end of the natural intact femur. Furthermore, this emulation is accomplished by replacing with mechanically equivalent structure only what has actually been removed from the femur. Therefore, damage to the natural bone due to the surgical procedure is kept to a minimum. Since the components of the natural bone are replaced by such mechanical equivalent structures, the coupling of different loads at the various interfaces with the remaining bone are minimized. Consequently, the stresses on the remaining intact femoral structure are more or less the same as in the natural bone. Therefore, that remaining structure does not tend to degenerate with time so that the implant remains firmly fixed in the femur of even a young patient. Finally, because implantation of the prosthesis components can occur without employment of any cement, immediate post surgical fixation of the prosthesis occurs so that the patient is ambulatory very shortly after the operation.

Figure 6:
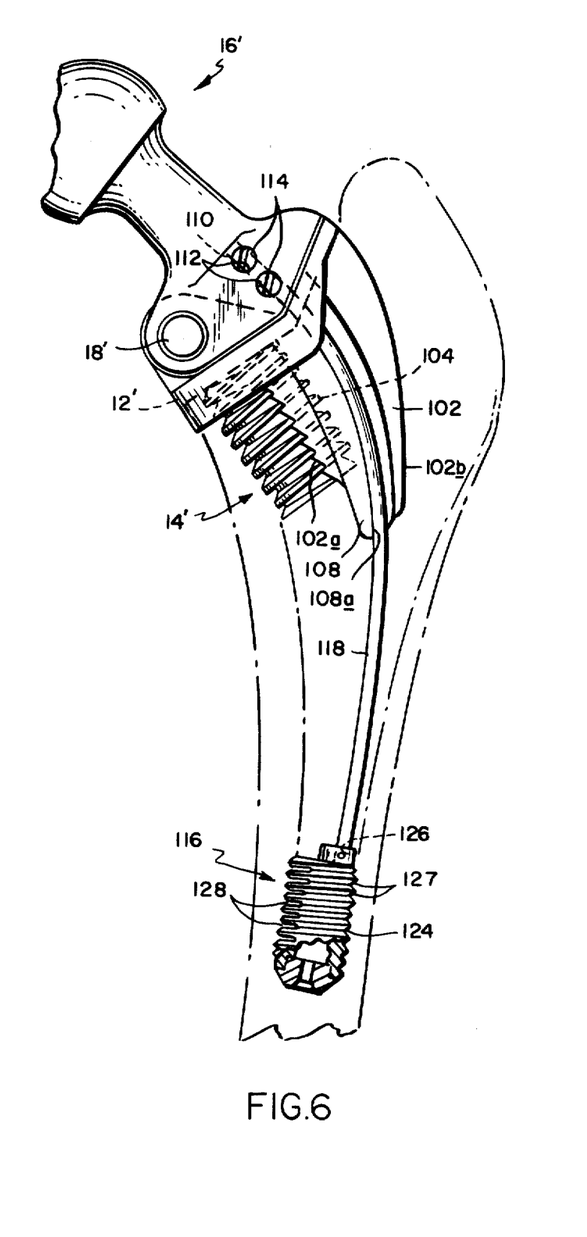
FIG. 6 is a view similar to FIG. 3 of another embodiment of my femoral prosthesis.
Figure 6A:
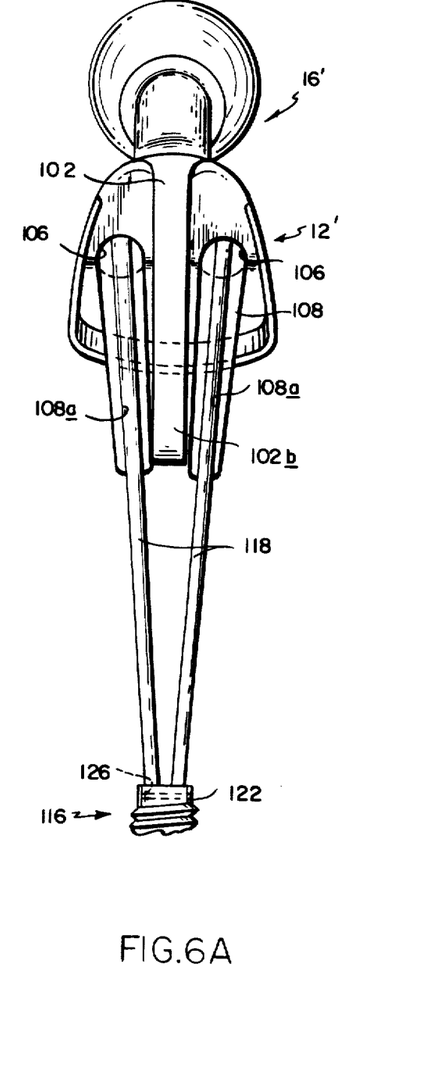
FIG. 6A is a rear elevational view thereof with parts broken away.
Figure 6B:
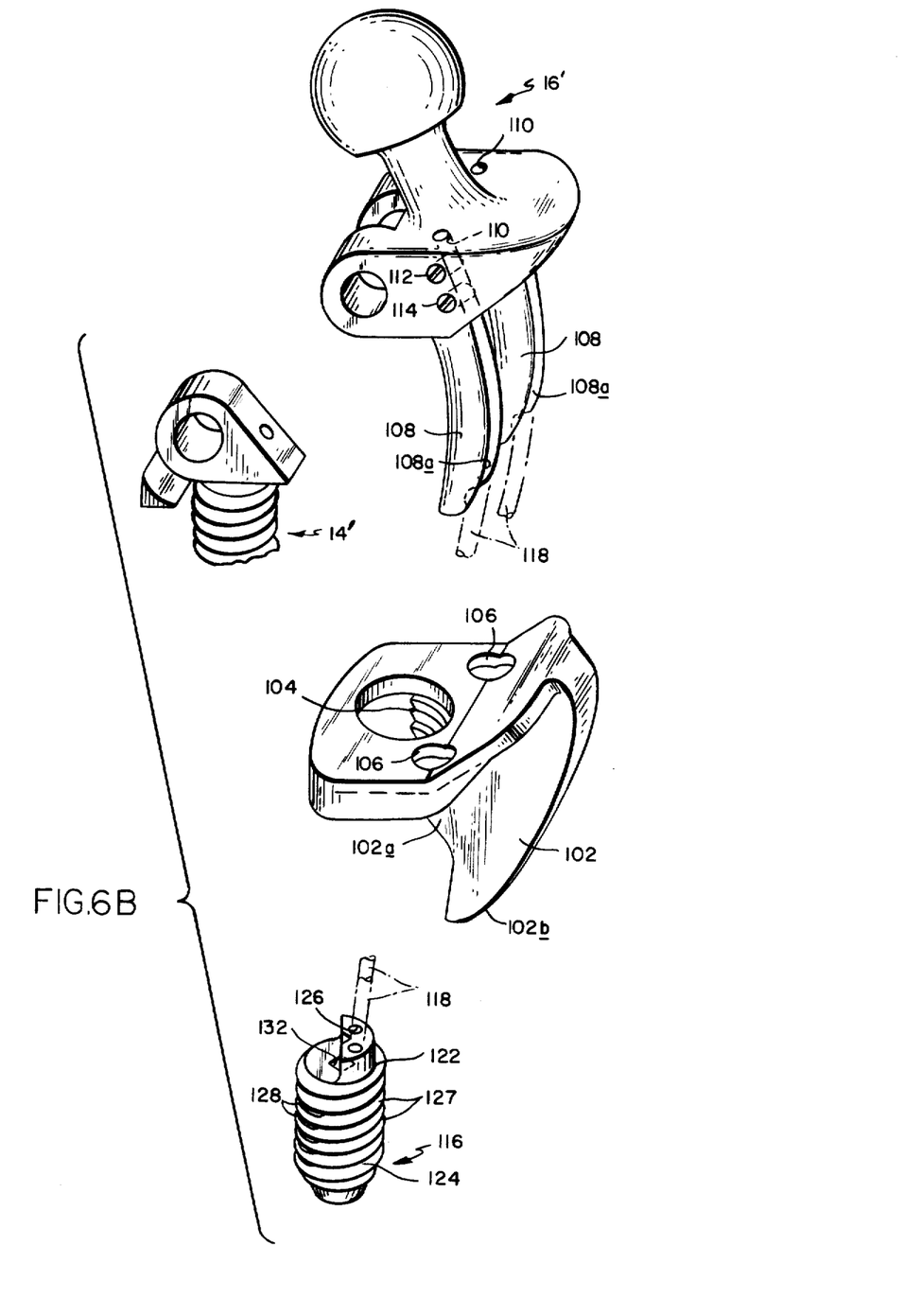
FIG. 6B is an exploded perspective view showing the component of the FIG. 6 prosthesis in greater detail.

In some patients, the condition of the cancellous bone in the proximal end of the femur is so damaged that it may be judged unsatisfactory for bedding the anchoring wires 22. In this event, it would be desirable for the femoral prosthesis to couple the tensile component of the load directly to the lateral side of the femoral shaft S. Such an implant is illustrated in FIGS. 6, 6A and 6B. The basic difference between this prosthesis and the one depicted in FIG. 3 resides in its structure for transmitting the tensile component of the load from the head of the prosthesis to the lateral side of the femur. Therefore, only the differences will be discussed in detail.

The FIG. 6 implant comprises a base plate 12', a compression screw 14' and a head member 16'. The compression screw may be identical to screw 14 described above. The base plate is somewhat different from its FIG. 3 counterpart in that it has no key 36 or wire passages 38. Instead, a centrally located leg 102 extends down from the lateral section of the plate. The medial edge 102a of that leg is essentially vertical and located just to the right of the screw opening. Furthermore, that edge is provided with thread segments 104 which are shaped to receive the threaded shank of screw 14' when it is screwed down through the plate opening. The lateral edge 102b of leg 102 curves down from the lateral end of the plate to the lower end of leg edge 102a. In this, that edge corresponds more or less to the shape of the lateral side of the femoral medullary canal into which the plate is placed as shown in FIG. 6.

Further, unlike plate 12, plate 12' has a pair of relatively large openings 106 extending down through its lateral section on opposite sides of leg 102.

Referring to FIGS. 6 to 6B, the prosthesis head member 16' differs from member 16 described above in that it has no keyway 84 in its underside. Rather, a pair of long, spaced-apart, claw-shaped fingers 108, the curvatures of which correspond more or less to the lateral edge 102b of the base plate leg extend down from the lateral end of its shoulder section. The lateral face of each finger 108 is formed with a lengthwise channel or groove 108a for reasons that will become apparent. Also, a more or less vertical passage 110 extends up from the underside of the head member 16' in line with each finger groove 108a. A pair of tapped holes 112 are formed through the wall of each such passage 110 for receiving set screws 114.

In the FIG. 6 implant embodiment, the anchoring wires 22 (FIG. 3) are substituted for by an anchoring screw indicated generally at 116 and anchoring cables 118 connected between the anchoring screw and the head member 16'. More particularly, because in this example there is insufficient material in the proximal femur to retain the anchoring wires 22, the anchoring screw 116 is screwed down deep into the hollow medullary canal as shown in that drawing figure.

Screw 116 comprises a head 122 and an exteriorly threaded shank 124. The head is formed with sockets 126 at the lateral side thereof containing the lower ends of cables 118. The cables can be retained in the sockets by any suitable means such as welds, brazes, set screws or the like. The screw shank 124 is very similar to the shank 48 of screw 14 depicted in FIG. 5B. It differs in that its screw thread 127 is upwardly cupped and the shank is slotted on its medial side at 128 to make the thread convolutions compliant on that side of the shank rather than on the lateral side thereof as is the case with screw 14.

The anchoring screw 116 with the cables 118 attached is screwed down into the medullary canal preferably using a long flexible key or wrench (not shown) whose end engages in a noncircular recess 132 in the top of the screw head 122. The insertion process can be facilitated if a sleeve (not shown) is inserted down into the femoral canal around the cables to prevent the cables from becoming tangled inside the canal as the screw is being turned.

When properly inserted, the screw thread 127 bites into the lateral wall of the cortical tube. The sockets 126 and the cables 118 are located as far as possible to the lateral side of the tube so that tensile forces are coupled to that side of the femur. As noted previously, the thread convolutions on the medial side of the screw are compliant so that minimal tensile force is coupled to the medial side of the femur in order to emulate as much as possible the forces imposed upon the natural femur.

After the anchoring screw 116 is in place with the cables 118 extending out of the proximal end of the femur, the base plate 12' is seated on the end of the femur with its leg 102 extending down into the medullary canal so that the curved leg edge 102b engages the lateral side of the cortical tube as best shown in FIG. 6. Next, the compression screw 14' is screwed down through the plate opening into the proximal femur between the medial femoral wall and plate leg 102. As noted previously, the medial edge 102a of that leg is threaded so that, as the screw 14' is turned down along those thread segments, the screw threads are also constrained to bite into the bone matter at the medial side of the cortical tube as shown in FIG. 6. When the screw 14' is fully inserted, its reduced diameter neck is opposite the threaded plate opening so that the screw is no longer axially coupled directly to the plate. Also, the screw is oriented so that the screw head opening is positioned at the medial side of the screw which places the compliant convolutions of the screw thread 127 engage the threaded edge 102a of the plate leg 102. Accordingly, any compressive forces applied to screw 14' are coupled to the medial side of the femur rather than to the plate leg.

Next, the head member 16' is positioned opposite the plate member with its fingers 108 projecting loosely down through the plate openings 106 therein. Also, the cables 118 are threaded up through those openings and through the passages 110 in the head member as that member is seated against the plate with its ear passages aligned with the passage in the screw head. A pin 18' identical to pin 18 depicted in FIG. 3 can now be inserted into those passages to pivotally lock the head member 16' to the compression screw 14'. Finally, the upper ends of the cables 118 are pulled through the head member passages 110 until the cables are taut. The cables are then secured to the head member by tightening the set screws 114. Any excess cable projecting from the upper ends of the passages 110 can be cut away.

The FIG. 6 prosthesis functions under load in the same way as the one described in FIG. 3. Downward force on the head member 16' results in the compressive component being coupled by pin 18' and compression screw 14' to the medial side of the proximal femur. The tensile component of the downward force is coupled from the head member by way of the cables 118 and anchoring screw 116 to the lateral side of the femur shaft, the compression due to that force also being transmitted to the screw which receives no tilting moments due to its pivot at pin 18' and secondarily to plate 12'.

The tension on the cables 118 also maintains the position of the plate leg 102 so that the shank of the screw 14 is held tightly against the medial side of the cortical wall. Therefore, this prosthesis, like the one illustrated in FIG. 3, emulates in a one-to-one manner the physical locations and functions of the natural structural components of the femur. Therefore, the pattern of the load transfer and the resulting stresses developed in the femur should closely resemble those of the intact structure exactly as is the case with the FIG. 3 implant so that the remaining bone structure should remain healthy and strong.

While we have shown two different embodiments of the femoral implant, it should be apparent that, in some situations, a combination of the two structures might be employed advantageously. In other words, the condition of the proximal femur of a particular patient might warrant an implant employing both the anchoring wires 22 and one or more cables 118 anchored by a screw 116. Such a hybrid prosthesis would have the advantages of both of the implants described above.

Indeed, as the two embodiments employ the same compression screw 14, they could be designed to utilize the same basic base plate. That is, the base plate shown in FIG. 5A could be designed so that the section of that plate containing key 36 could itself be keyed to the remainder of the plate member so that, when cables 118 are used, that portion could be removed and replaced by another key member containing the openings 106 and depending leg 102. In a similar manner, the head member fingers 108 could be formed at their upper ends with a common key which slides into the keyway at the underside of the head member depicted in FIG. 5C.

The same principles are followed to design and implant an acetabular component of a total hip joint. More particularly an acetabular prosthesis or cup made in accordance with my technique, comprises a flexible cup or socket liner, formed of thin titanium metal or the like. The outside surface of the liner is covered with a compressive material such as honeycomed or rippled titanium to provide an interface between the liner and the remaining, subchordal plate in the hip bone. The stiffness of that outside layer is more or less the stiffness equivalent of the removed thickness of the subchordal plate. That layer should also provide a bone ingrowth layer for tissue. In this way, the remaining cancellous bone material in the socket is compressed in the same manner as in the natural hip bone with substantially no shear forces being applied to it.

Preferably, also, a relatively stiff lip is provided around the liner to load the remaining cortical shell around the socket as is done in the natural hip bone. In other words, the cup lip applies a more or less radial force on the cortical bone around the lip of the socket to emulate the normal hip joint and thus minimize degeneration of the remaining bone around the socket. Other artificial joints such as leg and arm joints can be fabricated and implanted in more or less the same way to minimize the need for joint replacement and to maximize the life of the prostheses and of the natural bones in which they are implanted.

Figures 7, 7A, 7B:
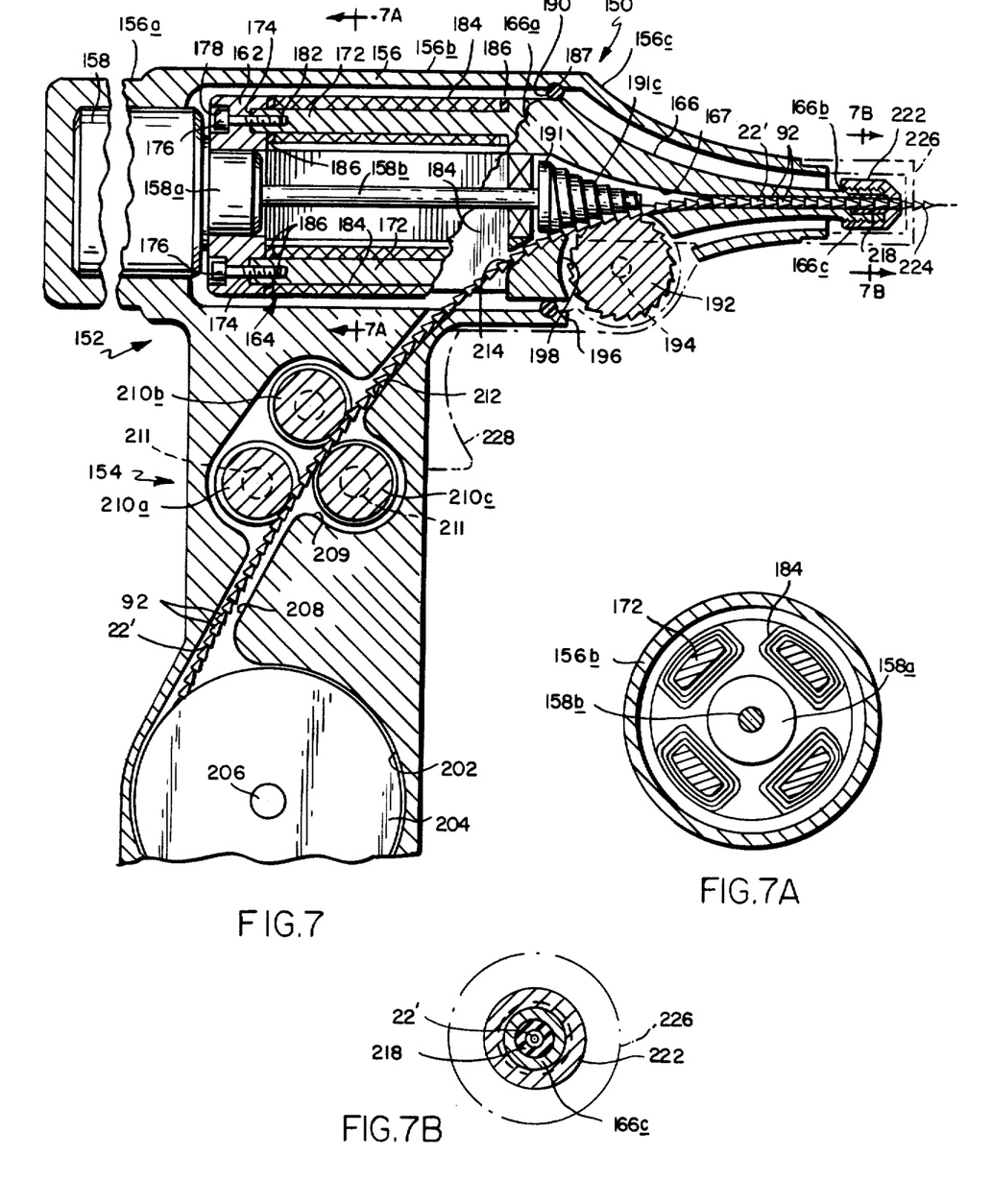
FIG. 7 is a longitudinal sectional view with parts in elevation showing apparatus for installing the anchoring wires incorporated into the FIG. 3 prosthesis.
FIG. 7A is a sectional view along line 7A—7A of FIG. 7.
FIG. 7B is a sectional view on a larger scale along line 7B—7B of FIG. 7.

It is desirable that the anchoring wires 22 in the prosthesis depicted in FIG. 3 be inserted into the femur under a constant force and without causing undue damage to the bone tissue. FIGS. 7 to 7B illustrate a tool which is specifically designed to accomplish that. The tool shown generally at 150 in FIG. 7 provides a constant insertion force along the anchoring wire 22' and applies a simultaneous ultrasonic vibration to the wire which greatly reduces the force of the insertion into the femur, thereby minimizing damage to the bone and increasing the strength of the anchor created by the wires.

Tool 150 comprises two main parts, to wit: a head indicated generally at 152 and a pistolgrip-like handle 154 which depends from the head. The head includes a generally cylindrical housing 156 composed of a left-hand end section 156a, a central section 156b and a right-hand funnel-like section or nozzle 156c which constitutes the working end of the tool.

An electric motor 158 is snugly seated in housing section 156a. The motor has a reduced diameter 158a which projects into housing section 156b. Engaged around the neck is a mounting collar 162 which is fixed in the radial direction relative to the motor but is free to slide axially to some extent along its neck 158a.

Positioned in housing sections 156b and 156c is a magnetorestrictive ultrasonic transducer shown generally at 164. The transducer includes a horn section 166 having a relatively large mouth or entrance end 166a positioned at the right hand end of the housing section 156b. The horn follows the general contour of housing section 156c with its small end 166b projecting out through the open working end of the housing. The horn has an internal passage 168 which is relatively large at the mouth of the horn and reduces gradually to a small opening at the horn end 166b which is only slightly larger than the diameter of the anchoring wire 22'.

As best seen in FIGS. 7 and 7A, projecting axially from the entrance end of the horn is a circular array of four generally rectangular legs 172 which function as transducer armatures. The free ends of these armatures extend into recesses 174 spaced around the opposing face of the mounting ring 162. The transducer 164 is secured to the mounting ring 162 by countersunk bolts 176 extending through counterbored axial openings 178 in the mounting collar and turned down into threaded openings 182 in the ends of the armatures 172. Prior to mounting the armature 164 to the mounting collar 162, a wire coil 184 is slid onto the end of each armature with appropriate insulating washers 186 being provided at the coil ends.

Thus by its connection to motor 158, the left end of the transducer 164 is fixed radially, but free to slide to some degree axially with housing 156. The radial position of the transducer horn is maintained by a resilient gasket 187 which encircles the horn mouth 166a. The gasket is seated in a circular groove 190 inscribed in the inside wall of housing section 156b adjacent the right-hand end thereof. While establishing the radial position of the right-hand end of transducer 164 in the housing 156, the gasket does permit the transducer to undergo vibratory motion in the axial direction within the housing.

The motor 158 has a shaft 158b which extends axially between the armatures 172 into the mouth of the horn 166 being terminated therein by a frustoconical gear 191 having a spiral thread 191a. An idler gear 192 pivoted at 194 to the wall of housing section 156c is spaced opposite gear 191. Appropriate openings or recesses 196 and 198 are provided in the undersides of the housing section 156c and the transducer horn 166 respectively to provide clearance for gear 192.

Still referring to FIG. 7, a lateral recess 202 is provided in the tool handle 154 for loosely receiving a spool 204 of anchoring wire 22'. The spool is rotatively mounted on a pivot 206 projecting laterally from the handle 154 into recess 202 so that the spool is free to rotate in the recess. The spool 204 can be supplied in a suitable package which is presterilized with the wire 22' being prebent so that, when the wire is released from the spool, it has a curvature which is slightly less than that of the trabeculae B depicted in FIG. 1.

The wire 22' from the spool is threaded through a passage 208 extending along the handle from recess 202 to a second lobed recess 209 near the top of the handle. That recess contains a set of three rollers 210a, 210b and 210c which are rotatively mounted on axles 211 projecting from the handle 154 into recess 209. Two of the rollers 210a and 210b are spaced apart along a line extending generally parallel to the course of the wire 22' through recess 209. The third roller 210c is positioned on the opposite side of the wire opposite the space between the first two rollers. Roller 210c or more particularly its pivot 211 is adjustable by conventional means (not shown) toward and away from rollers 210a and 210b to provide a fine adjustment of the bending of the wire 22' drawn from spool 204.

The anchoring wire 22' threads from the rollers through a passage 212 leading from recess 209 into the housing section 156b. Thence the wire passes through the gap between a pair of the transducer coils 184 into a passage 214 in the underside of the horn mouth 166a. Passage 214 leads into the nip between gears 191 and 192 inside the horn passage 167. The shape of the thread on gear 191 is such that it meshes with the frustoconical wire sections 92 in the same manner as a worm gear drive. When motor 158 is energized, it tends to turn gear 191 in a direction that draws wire 22' from spool 204 (herein the counterclockwise direction). As we shall see, however, the wire is not actually drawn from the spool in that fashion.

The wire leaving the gears is pushed through the horn passage 167 to the horn end 166b. It should be mentioned at this point that all of the recesses 196, 198, 202 and 209 are provided with appropriate covers (not shown) which enclose the components in those recesses yet permit easy access to them for replacement and repair purposes.

Referring now to FIGS. 7 and 7B, an exteriorly threaded tubular enlargement 166c is formed at the horn end 166b. Positioned in that enlargement is a tubular sleeve 218. The sleeve is made of a plastic material, for example, and has a bore which snugly receives wire 22'. The sleeve is held in place by an interiorly threaded cap 222 which is screwed onto the threaded enlargement 166c. The cap has an end opening 224 aligned with the passage through sleeve 218 so that the wire drawn from the spool 204 can be pushed out through that opening.

If desired, the working end of the tool can be provided with an appropriate end cap to protectively enclose the horn end 166b, such a cap being shown in dotted lines at 226 in FIG. 7. The motor 158 and the coils 184 of transducer 164 are connected to an appropriate power source by way of a trigger switch shown in dotted lines at 228 in FIG. 7.

When the tool 150 is energized, the motor 158 acting through gear 191 applies a static force to wire 22'. At the same time, transducer 164 is energized so that it undergoes vibratory motion in the axial direction. Due to its horn 166, the amplitude of these vibrations is maximized at the horn end 166c containing sleeve 218. That sleeve which tightly encircles the wire 22' couples the vibratory motion of the horn to the anchor wire.

Due to the asymmetric frustoconical shape of wire sections 92, forward motion of the horn end 166c is transmitted by the sleeve 218 to the wire better and more efficiently than is the rearward motion of that horn end. Therefore, there is a net force on the wire tending to advance it out of the tool. The sleeve 218 wears out relatively quickly due to its tight engagement with the wire 22' and therefore should be replaced fairly often e.g., each time the wire spool 204 is replaced.

Wire 22' would feed from the working end of the tool 150 even if a static force were not applied to the wire by the motor-driven gear 191. Generally, however, enough static force is applied by the motor 158 to overcome the frictional forces tending to retard advancement of the wire out of the tool. In other words, the force of the motor drive alone is desirably just barely sufficient to push the wire from the tool.

To use the tool, trigger switch 228 is closed so that a section of wire 22' is ejected from the tool. The curvature of that section is checked against the X-rays of the particular patient and the roller 210c is readjusted toward or away from rollers 210a and 210b until the desired curvature is obtained to match the curvature of the patient's trabeculae B (FIG. 1).

The cap 226 at the working end of the tool is pressed against the base plate section 26a (FIG. 4) so that the cap opening 224 is aligned with one of the openings 38 in the base plate. Then the tool is actuated so that the wire 22' is driven through that opening and down into the bone as shown in FIG. 4. Usually the ultrasonic vibrations imparted to the wire are sufficient to drive the wire into the bone. However, if resistence is encountered, additional power can be supplied to the motor 158 to increase the static insertion force imparted to the wire 22' by driven gear 191. In any event, accomplishing the wire 22' insertion by ultrasonic vibration greatly reduces the force of the insertion and minimizes damage to the bone. The end result is that the wire provides a stronger anchor between the prosthesis base plate 12 and the femur.

It will be appreciated that the working end of the tool can be modified to include mechanisms for dispensing the split collars 94 (FIG. 5D) and for cutting the wire 22' above the collar after its insertion into the bone as described above. Also, while the tool 150 is specifically adapted to dispense anchoring wires for hip prosthesis fixation, the same or a similar tool can be used to dispense and apply wire for other surgical procedures. For example, such a tool can be used to apply wire used to tie together sections of bone, etc.

Also, certain modifications may be made in the above described tool to reduce its size and simplify its construction. For example, the motor 158 and transducer 164 can be combined into one unit with the ultrasonic transducer coil being integrated into the motor armature. Also, the vibration-coupling sleeve 218, instead of being made of plastic, can comprise a fibrous structure whose fibers are oriented forwardly in a fishbone fashion so that the forward motion of the transducer 164 is coupled even more effectively to the wire 22'.

It will be seen from the foregoing that my hip joint prostheses and ancillary tool for inserting wire for anchoring the prostheses are significant improvements over comparable present day apparatus of these types. Therefore, they should make hip surgery much simpler, safer and more permanent for many patients, particularly young patients who have to rely on the prostheses for a prolonged period.

It will thus be seen that the objects set forth above, among those made apparent from the preceding description, are efficiently attained, and, since certain changes may be made in the above method and in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. Prosthesis apparatus comprising
  A. a base plate for engaging flush against a prepared part of a bone;
  B. at least one elongated flexible substantially inextensible tension transmitting means having one end extending to said plate and its opposite end arranged to be anchored inside said bone at a first location therein normally subjected to tension forces;
  C. a joint member positioned against said base plate;
  D. connecting means for connecting a first part of said joint member to said one end of said tension transmitting means;
  E. compression transmitting means for transmitting compressive loads on said first member to bone, said compressive transmitting means including a first portion for anchoring inside said bone adjacent said plate at a second location therein different from said first location and normally subjected to compression forces and a second portion extending to said joint member through said plate;
  F. coupling means for coupling a second part of the joint member to said second compression transmitting means portion so that a normal load applied to the joint member is reduced to a compression force on the compression transmitting means; and
  G. decoupling means for decoupling the plate from the compression forces applied to the compression transmitting means.

2. The apparatus defined in claim 1 wherein
  A. the base plate has first and second substantially planar surfaces which intersect to form an included angle of 90° to 180°,
  B. said tension transmitting means one end extends to said first plate surface, and
  C. said second compression means portion extends through said second plate surface.

3. The apparatus defined in claim 2 wherein the included angle is about 110°.

4. The apparatus defined in claim 1 wherein the base plate has a depending skirt around at least a part of the plate periphery.

5. The apparatus defined in claim 1 wherein the surface of the plate facing the bone part is coated with promoting means for promoting bone ingrowth.

6. The apparatus defined in claim 1 wherein the tension transmitting means comprise a plurality of flexible wires.

7. The apparatus defined in claim 6 wherein the wires have corresponding first ends connected to the base plate.

8. The apparatus defined in claim 7 wherein
  A. the base plate is formed with a plurality of small passages therethrough; and
  B. the first ends of the anchoring wires extend into the passages.

9. The apparatus defined in claim 8 and further including engagement means engaging around the first ends of the wires for wedging the wire ends into said plate passages to connect them to the plate.

10. The apparatus defined in claim 9 wherein
  A. each wire is composed of a string of conical sections; and
  B. the engaging means comprise a collar engaged around one section of each said wire for wedging into a said plate passage.

11. The apparatus defined in claim 1 wherein the tension transmitting means comprise a plurality of flexible wires having barbs projecting away from the base plate.

12. The apparatus defined in claim 1 wherein the tension transmitting means comprise
  A. one or more flexible inextensible wires; and
  B. anchoring means for anchoring the end of each wire distal inside the plate to the bone.

13. The apparatus defined in claim 12 wherein the anchoring means comprise a threaded fastener for screwing into the structure of the bone.

14. The apparatus defined in claim 13
  A. wherein the fatener has a thread that is cupped toward said one or more wires; and
  B. further including fastener-engaging means formed in a surface of the fastener facing said one or more wires.

15. The apparatus defined in claim 13 wherein
A. the fastener has a tubular shank; and
B. the screw thread convolutions on one side of the shank are more axially compliant than the screw thread convolutions on the opposite side of the shank.

16. The apparatus defined in claim 1 wherein the connecting means comprise
A. fixing means fixing said one end of the tension transmitting means to the plate; and
B. joining means for joining said plate to said first part of the joint member at the general location of said fixing means.

17. The apparatus defined in claim 16 wherein the joining means comprise a keying connection between the head member and the plate.

18. The apparatus defined in claim 1 wherein the compression transmitting means comprise a relatively short rigid screw member having a head coupled to said head member and a shank for screwing into said bone.

19. The apparatus defined in claim 18 wherein the shank thread segments on one side of the shank are more axially compliant than the thread segments on the opposite side of the shank.

20. The apparatus defined in claim 19 wherein
A. the shank has a thread that is cupped away from the screw member head; and
B. the relatively more compliant thread segments are arranged to be aligned generally with the coupling means.

21. The apparatus defined in claim 18 wherein
A. the screw member shank is tubular; and
B. the free end of the shank is formed with cutting edges to cut bone matter when the shank is screwed into said bone.

22. The apparatus defined in claim 1 wherein the coupling means comprise pivot means defining a pivot joint between the head member and the second compression transmitting means portion.

23. The apparatus defined in claim 1 wherein the decoupling means comprise means a sliding connection between the compression transmitting means and the plate which prevents movement of the compression transmitting means parallel to the plate plane through which it extends, but permits movement of the compression transmitting means perpendicular to said plate plane.

24. The apparatus defined in claim 23 wherein the coupling means comprise a pivotal connection between the joint member and the compression transmitting means.

25. The apparatus defined in claim 24 wherein the connecting means comprise
A. fixing means for fixing said one end of the anchoring means to said base plate; and
B. joining means for releasably joining said first part of said joint member to said plate.

26. The apparatus defined in claim 1 wherein said compression transmitting means comprise a screw member having
A. a head; and
B. an exteriorly-threaded tubular shank, the thread convolutions at one side of said shank being more axially compliant than the thread convolutions at the opposite side of said shank.

27. The apparatus defined in claim 26 and further including

A. opening defining means defining an opening through the head of the screw member; and
B. passage defining means defning at least one passage extending through a wall of said shank.

28. Prosthesis apparatus comprising
A. a joint member for mounting to a bone;
B. elongated inextensible but flexible tension transmitting means having one end portion arranged to be anchored inside said bone at a first location therein normally subjected to tension forces;
C. connecting means for connecting the opposite end portion of the tension transmitting means to the joint member at a first location thereon;
D. compression transmitting means for transmitting compressive loads on said joint member to said bone, said compression transmitting means having one end portion arranged to be anchored inside said bone at a second location therein different from said first location and normally subjected to compression forces; and
E. coupling means for coupling the opposite end portion of the compression transmitting means to the head member at a second location thereon different from said first location thereon.

29. The apparatus defined in claim 28 wherein the tension transmitting means comprise one or more flexible wires.

30. The apparatus defined in claim 29 wherein said one end portion of each wire is barbed.

31. The apparatus defined in claim 29 wherein the tension transmitting means also comprise means for anchoring said one end portion of each said one or more wires to said bone.

32. The apparatus defined in claim 31 wherein said anchoring means comprise a threaded fastener.

33. The apparatus defined in claim 28 wherein the joint member comprises a ball joint.

34. The apparatus defined in claim 28 wherein the compression transmitting means include a screw member having
A. a head coupled to the joint member by the coupling means; and
B. an exteriorly threaded shank screwed into the bone.

35. The apparatus defined in claim 34 wherein the coupling means comprises a pivotal connection between the joint member and the screw member.

36. The apparatus defined in claim 29 wherein the connecting means comprise
A. a plate member;
B. fixing means for fixing the opposite end portion of each said wire to said plate member; and
C. joining means for removably joining said joint member first location to the plate member at the general location of said fixing means.

37. The apparatus defined in claim 36 wherein the compression transmitting means comprise a screw member extending through the plate member at a location therein spaced from said fixing means.

38. A prosthesis insertion method comprising the steps of
A. cutting a bone that is to receive a prosthesis along one or more cut planes extending generally perpendicular to the bone trabeculae which are subjected to tension and compression forces by a normal load on the bone;
B. covering the cut planes with a base member;

C. inserting one or more flexible inextensible anchoring strands through the base member into a first portion of the bone containing trabeculae normally subjected to tension forces;

D. inserting a compression resistant member through the base member into a second portion of the bone different from the first portion and normally subjected to compression forces;

E. positioning a joint member on the base member;

F. connecting the proximal ends of the strands to the joint member at a first location thereon; and G. rotatively coupling the compression resistant member to the joint member at a second location thereon so that only compression forces are transmitted from the joint member to the compression resistant member.

39. The method defined in claim 38 and including the additional step of providing play between the base member second location and the compression resistant member.

* * * * *